United States Patent
Wagner et al.

(10) Patent No.: US 9,687,472 B2
(45) Date of Patent: Jun. 27, 2017

(54) USE OF ANTIOXIDANTS AS AN ADJUVANT TO IMMUNE STIMULATORS TO AUGMENT TUMOR IMMUNITY AND PREVENT TOXICITY ASSOCIATED WITH OXIDATIVE STRESS

(71) Applicant: BATU BIOLOGICS, San Diego, CA (US)

(72) Inventors: Samuel C. Wagner, San Diego, CA (US); Andy J. Kim, San Diego, CA (US); Dimitri N. Theofilopoulos, San Diego, CA (US); Brandon R. Dolan, San Diego, CA (US); Naseem Ajili, Laguna Niguel, CA (US)

(73) Assignee: Batu Biologics, San Diego, CA (US)

( * ) Notice: Subject to any disclaimer, the term of this patent is extended or adjusted under 35 U.S.C. 154(b) by 0 days.

(21) Appl. No.: 14/706,238

(22) Filed: May 7, 2015

(65) Prior Publication Data

US 2015/0342925 A1    Dec. 3, 2015

Related U.S. Application Data

(60) Provisional application No. 61/990,231, filed on May 8, 2014.

(51) Int. Cl.
| | | |
|---|---|---|
| *A61K 31/375* | (2006.01) | |
| *A61K 9/00* | (2006.01) | |
| *A61K 31/355* | (2006.01) | |
| *A61K 31/4745* | (2006.01) | |
| *A61K 38/20* | (2006.01) | |
| *A61K 31/437* | (2006.01) | |
| *A61K 45/06* | (2006.01) | |

(52) U.S. Cl.
CPC .......... *A61K 31/375* (2013.01); *A61K 9/0019* (2013.01); *A61K 31/355* (2013.01); *A61K 31/437* (2013.01); *A61K 31/4745* (2013.01); *A61K 38/2013* (2013.01); *A61K 45/06* (2013.01)

(58) Field of Classification Search
None
See application file for complete search history.

(56) References Cited

U.S. PATENT DOCUMENTS 5,508,031 A * 4/1996 Zimmerman ........ A61K 38/191
                                                  424/85.2
7,071,158 B2 * 7/2006 Chinery ................ A61K 31/00
                                                  514/1

* cited by examiner

*Primary Examiner* — Brian J Davis
(74) *Attorney, Agent, or Firm* — Hankin Patent Law, APC; Susan L. Mizer; Anooj Patel

(57) ABSTRACT

The current application teaches methods and compositions useful for the treatment of cancer through administration of an antioxidant together with an immune stimulator at concentrations sufficient to augment antitumor immunity while simultaneously preventing inhibition of T cell function as a result of tumor secreted oxidative stress. Compositions such as toll like receptor agonists in combination with antioxidants are disclosed. In further embodiments, the application teaches the use of antioxidants to prevent immunotherapy associated oxidative stress, of which, one manifestation is vascular leak syndrome. In one specific embodiment, the application teaches the use of intravenous ascorbic acid as a means of reducing IL-2 associated toxicity.

9 Claims, 1 Drawing Sheet

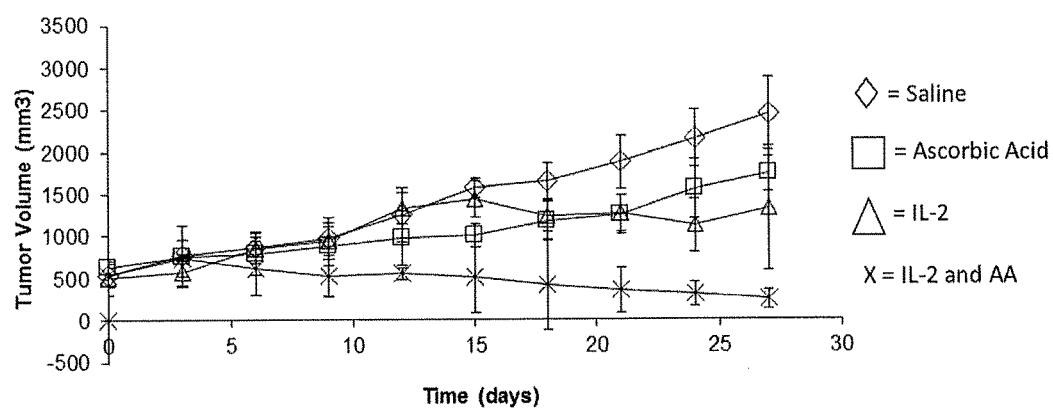
Synergistic Reduction in Tumor Growth by IL-2 and Intravenous Ascorbic Acid

USE OF ANTIOXIDANTS AS AN ADJUVANT TO IMMUNE STIMULATORS TO AUGMENT TUMOR IMMUNITY AND PREVENT TOXICITY ASSOCIATED WITH OXIDATIVE STRESS

CROSS-REFERENCE TO RELATED APPLICATION

This application claims the benefit of U.S. Provisional Application No. 61/990,231 filed on May 8, 2014, the contents of which are incorporated by reference herein in its entirety.

TECHNICAL FIELD

This application relates to the area of anticancer therapeutics, more specifically, the application relates to the area of cancer immunotherapy. Specifically, the application discloses means of decreasing toxicity associated with immunotherapeutic interventions, while concurrently augmenting immune mediated inhibition of cancer growth and progression.

BRIEF SUMMARY

The current application teaches the use of a stimulator of immunity together with an antioxidant for augmentation of efficacy and reduction of toxicity associated with administration of said immune stimulator. In one embodiment, IL-2 is utilized as an immune stimulator, while intravenous ascorbic acid is utilized as an antioxidant. In another embodiment, TLR activation in combination with an antioxidant is employed for synergistic enhancement of immune response, as well as tumor cell killing. In one embodiment, administration of the TLR-7 agonist imiquimod is performed in combination with ascorbic acid at a concentration sufficient to induce antitumor effects. In another embodiment, an antioxidant is administered intravenously with imiquimod for protection of the endothelium from imiquimod mediated toxicity, while allowing immune enhancement.

BRIEF DESCRIPTION OF THE DRAWING

FIG. 1 is graph illustrating the synergistic reduction in tumor growth over time resulting from the administration of IL-2, ascorbic acid, and both as compared to saline.

DETAILED DESCRIPTION

The basis of cancer therapy is to identify/develop interventions that: a) selectively kill tumor cells while sparing non-malignant cells; b) prevent development of tumor-resistance; and c) act systemically to prevent relapse. Theoretically, immunotherapy of cancer would achieve all these aims. Selective killing of tumor cells has been demonstrated by a wide range of immune cells ranging from conventional CD8 T cells, gamma delta T cells, natural killer (NK) cells, natural killer T (NKT) cells and in some studies neutrophils. Other components of the immune system expressing tumor selectivity include complement factors and natural antibodies of the IgM isotype. Tumor resistance to immunotherapy, differs from resistance to chemotherapy, where expression of multiple drug resistance proteins actively pumps out cancer-toxic substances. One mechanism is downregulation of human leukocyte antigen (HLA) by tumor cells in response to T cell killing. The immune system conceptually overcomes this by the NK subset which preferentially kills cells with downregulated HLA. The other mechanism of tumor resistance from immunological attack is by mutating antigens that are being recognized. Given the promiscuous binding ability of T cell and B cell receptors to bind antigens, the cells could conceptually "mutate with the tumor" in order to recognize and kill cells with variant antigens. Immunological destruction of neoplasia is believed to occur at a systemic level and thus arises the possibility to inhibit metastasis and tumor recurrence, in part through induction of immunological memory.

The history of tumor immunotherapy begins with the work of William Coley who induced a systemic inflammatory/immune activation through administration of killed *S. pyogenes* and *Serratia marcescens* bacteria in patients with soft tissue sarcoma. The advent of molecular biology allowed for assessment of molecular signals associated with systemic immune activation. The cytokine tumor necrosis factor (TNF)-alpha was one of the molecular signals associated with anticancer efficacy of innate immune activators such as the Coley vaccine. Studies have demonstrated that TNF-alpha has the ability to induce profound death of cancer cells in vitro and in vivo in animal models, however human studies demonstrated unacceptable levels of toxicity. IL-2 was the next cytokine associated with immune activation that was tested. Originally termed T Cell Growth Factor (TCGF), IL-2 was demonstrated in early studies to endow human lymphocytes with ability to selectively kill tumor but not healthy control cells. Subsequent studies have demonstrated that cytotoxic activity was mediated through T cell and natural killer (NK) cells, whose activation requires stimulation of the IL-2 receptor, which can be accomplished in vivo with high doses of IL-2. Animal studies suggested that IL-2 has a short half-life of approximately 2 minutes after intravenous injection, and human half life was reported to be approximately an hour. Thus it was apparent that clinical use of IL-2 would be requiring repeated administration at high doses. Despite this pitfall, preclinical studies demonstrated highly potent anti-tumor effect. In 1985 Steven Rosenberg reported regression of established pulmonary metastasis, as well as various subcutaneous tumors by administration of IL-2. These data were highly promising due to the fact that tumor killing could be achieved systemically, and by activation of specific immune cells that could be identified in vivo as interacting with and inducing death of the tumor.

Early studies of IL-2 demonstrated impressive results in a subset of melanoma and renal cell cancer patients. Development of systemic autoimmunity to melanocytes, such as the occurrence of vitiligo during the treatment with systemic IL-2 was found to be predictive of response. These studies were expanded and eventually IL-2 received approval as the first recombinant immunotherapeutic drug by the FDA. There appears to be a dose response with IL-2 in that the doses that seem to be most effective are also associated with significant toxicity. The most significant cause of toxicity is vascular leak syndrome (VSL), manifested as fluid loss into the interstitial space, which is a result of increase vessel permeability. Additional effects include thrombocytopenia, elevated hepatic serum transaminases, hepatocyte necrosis, hypoalbuminemia, tissue and peripheral eosinophilia, and prerenal azotemia. It is one of the aims of the current application to overcome IL-2 associated toxicities by the concurrent administration of ascorbic acid.

Vascular leak syndrome (VLS) is considered to be the major dose-limiting adverse effect of IL-2 administration. In a meta-analysis of studies performed in metastatic renal cell carcinoma patients, objective responses were observed in 23% of patients, the majority of which lasted more than 10 years. Unfortunately, 65% of patients have to interrupt or stop therapy because of VLS. This syndrome is characterized by an increased extracellular fluid extravasation, hypotension, ascites, pulmonary edema, and hydrothorax, and clinically resembles the systemic inflammatory response syndrome (SIRS). Dermatological manifestations include erythrematous eruptions and mild papillary edema associated with burning and pruritus of the skin. Severe forms of VLS are associated with pulmonary or cardiac failure with approximately 1% of treated patients having lethal outcome. Typically the symptoms of VLS are treated by vasopressor therapy and judicious fluid replacement, such as with colloid solutions for their osmotic effects. Patients may also be treated with theophylline and terbutaline, for which clinical experience suggests a possible reduction of the severity and frequency of acute episodes.

At a cellular level it is well-known that VLS is associated with endothelial cell activation and increased with vascular permeability. Biopsies of patients receiving IL-2 revealed an increased expression of adhesion molecules such as ICAM and LFA-1. These proteins are known to promote granulocyte extravasation, however, such upregulation was not observed when IL-2 was added directly to endothelial cell cultures in vitro, suggesting the effect was mediated by other host components. Given that one of the main cellular targets of IL-2 is the T cells, which express two types of IL-2 receptor, it appears that the initial T cell activation is a major contributor to downstream inflammatory effect on endothelium subsequent to IL-2 administration. In an early study, Rosenberg's group established a murine model for quantifying VLS by administering radioactively iodinated albumin into mice receiving IL-2 and assessing radioactivity of tissues. In this model, increased gamma-counts are correlated with endothelial permeability and leakage of albumin into tissues. They found that administration of IL-2 to nude mice or mice that have been immune suppressed by radiation, cyclophosphamide, or steroids, was associated with markedly reduced or no vascular leakage. It is within the scope of the current application to decrease IL-2 mediated T cell induction of endothelial activation by administration of antioxidants, such as ascorbic acid. In one embodiment of the invention ascorbic acid is combined with effective amounts of high molecular weight hyaluronic acid to decrease toxicity of IL-2 and allow for higher IL-2 administration. In one embodiment of the invention a deficiency of nutrients or micronutrients is corrected by supplementation with effective amounts of cysteine, methionine, calcium, magnesium, copper, zinc, iron, molybdenum, and selenium.

It is possible that the process of LAK generation is involved in stimulation of VLS, as was suggested in a study using a similar system in which transfer of LAK along with administration of IL-2 led to more profound endothelial leakage as compared to either alone. Interestingly, in the same study it was shown that depletion of host lymphocytes reduced vascular leakage only in response to IL-2 alone, but not in response to IL-2 and LAK transfer. Other studies have shown that cells bearing the NK marker asialo-GM1 are associated with some of the IL-2 associated toxicities. Anderson et al showed that antiserum to asialo GM1 suppressed mortality, vascular leak syndrome, hepatic damage and reduced infiltration of pulmonary and hepatic vasculature by asialo GM1+ lymphocytes induced by IL-2 treatment. Depletion of the Asialo-GM1 bearing cells did not alter lymphoid hyperplasia, tissue infiltration by Lyt 2+ lymphocytes, tissue and peripheral eosinophilia, or thrombocytopenia. Interestingly, the antisera did not affect the anti-tumor efficacy of IL-2 therapy in BDF mice bearing the colon 38 adenocarcinoma. Thus it is possible that T cell and NK cell activation by the high dose IL-2 induces production of various cytokines, one example being TNF-alpha, which are known to induce endothelial cell activation locally, and systemically are mediators of SIRS. Given that antioxidants have been successfully used in the treatment of SIRS, it is within the scope of the current application to apply antioxidants to the treatment of IL-2 mediated toxicity.

Another event associated with IL-2 administration appears to be complement activation. The complement system is an enzymatic cascade of about 30 circulating proteins, primarily generated by the liver that cause inflammation and amplification of a various immune responses. The complement system can be activated through the classical (antibody mediated) pathway, alternative pathways (antibody-independent), or through the mannose-binding lectin pathway, all of which lead to formation of the membrane attack complex which causes cell lysis through generation of pores in the cell membrane. In a clinical study of metastatic renal cancer patients receiving IL-2 via a 24-hour i.v. infusion at a daily dose of $3\times10(6)$ U/m$^2$ for 5 consecutive days, the classical complement pathway components C3 and C4 were measured daily during IL-2 infusion, and after its interruption. IL-2 administration was associated with a significant decrease in both C3 and C4 levels, which normalized on average 5 days after the end of IL-2 infusion. Another study associated presence of VLS in patients receiving IL-2 with complement activation as assessed by levels of C3a and the classical complement component C4a. In this study levels of C3a were as elevated as those found in septic and burn patients. Another study examining 23 cancer patients undergoing therapy with interleukin-2 and lymphokine-activated killer cells demonstrated 3-fold elevations of C3a desArg concentrations by the 8th day of therapy with concentrations of C4a desArg also being elevated by the end of therapy. Associated with activation of the complement system was an increase in the neutrophil cell-surface expression of complement receptor Type 1 and complement receptor Type 3.

This interesting dependence on T cells for complement activation bridges the studies demonstrating that T cells are necessary for both endothelial activation and VLS associated with IL-2 administration. A study by Vachino et al showed that cancer patients had pretreatment similar to control plasma levels of C3a, Ba, Bb, and SC5b-9. Post-IL-2 treatment C3a levels where shown to be increased on average of 15.6-fold. The Ba and Bb proteins, which belong to the alternatively complement activation pathway were augmented 8.0- and 5.0-fold, respectively, subsequent to IL-2 treatment. The plasma levels of the effector complement complex, SC5b-9, was increased 5.0-fold and the plasma C4d and iC3b concentrations increased 4.8- and 2.9-fold, respectively, after treatment. To show the involvement of patient lymphocytes in complement activation, the investigators found that cells expressing the T cell marker CD3 had increased surface expression of anti-C3c and anti-SC5b-9 by 6.2-fold and 5.1-fold, respectively after IL-2 therapy. The authors concluded that the T cells were participating in the IL-2 induced complement activation. This was also demonstrated in that increased concentration of the inflammatory protein C-reactive protein (CRP) was found post-IL-2 therapy, and that the T cells bound CRP. T cell bound CRP was capable of activating the alternative complement pathway. Therapeutically, it was demonstrated that administration of the complement inhibitor C1 esterase inhibitor was capable of reducing IL-2 induced hypotension and complement activation in patients.

Various components of the complement cascade have been demonstrated to directly activate endothelial cells, with endothelial cell activation not only causing lymphocyte and neutrophil extravasation, but also thrombosis by the upregulation of tissue factor. C5a is a byproduct of complement activation that has been demonstrated to induce endothelial cell activation and permeability. This protein is also a major effector in systemic inflammatory disorders and antibodies to it are being assessed clinically for this condition with some efficacy signals and suppression of endothelial activation published. The complement effector complex SC5b-9 was demonstrated in vitro to induce endothelial cell activation via stimulating expression of the Response Gene to Complement (RGC)-32, which in turn activates CDC2 and the AKT pathway. Jeffrey Platt's group demonstrated that complement activation is associated with induction of IL-1, which in turn stimulates endothelial cells expression of E-selectin, intracellular adhesion molecule-1, vascular cell adhesion molecule-1, Ikappa-Balpha, interleukin (IL)-1alpha, IL-1beta, IL-8, and tissue factor. Thus in the cascade of IL-2 induced VLS, it appears that T cell activation may be associated with complement activation, and complement activation, in turn, stimulates endothelial cell activation. One of the cardinal features of endothelial cell activation is stimulation of the clotting cascade.

According to the emerging picture that VLS has many common elements with SIRS, one of the common features is development of local thrombocyte and coagulation system activation. Innate immune response possesses the ability to locally marginalize pathogens by stimulation of clotting and consequent sequestration. However, this process becomes pathological when it occurs at a systemic level, such as SIRS or VLS. Upregulation of tissue factor expression was previously noted on endothelial cells from animals treated with IL-2. Expression of this protein is known to cause activation of the clotting cascade, as well as stimulate inflammatory processes. Hack et al demonstrated activation of the contact system of coagulation proteins by showing that patients on IL-2 therapy had degradation of factor XII and prekallikrein. Reductions in these proteins appeared not due to protein leakage into the interstitial space, since their levels were still significantly lower, i.e., 80 and 50%, respectively, when corrected for albumin decreases. Thus it appears that nonspecific activation of the coagulation system, and a resulting potential for thrombosis, occur as a result of IL-2 treatment. Given the inherently pro-thrombotic state of many cancer patients, it is theoretically possible that IL-2 therapy may have thrombotic complications, which indeed have previously been reported.

Granulocyte activation and tissue infiltration are hallmarks of systemic immune/inflammatory activation. In a study of 4 patients on IL-2, granulocytes became activated following IL-2 treatment with mean peak elastase/alpha 1-antitrypsin (E alpha 1 A) and lactoferrin values of 212 (SEM=37) and 534 (SEM=92) ng ml-1 respectively occurring 6 h after the IL-2. Activation of the complement cascade was evidenced by a dose dependent elevation of peak C3a values on day 5 of IL-2. The authors found that there was a significant correlation between C3a levels and the degree of hypotension during the first 24 h after IL-2 (r=0.91) and parameters of capillary leakage such as weight gain and fall in serum albumin (r=0.71). The authors concluded that activation of PMN initiates endothelial cell damage which subsequently leads to activation of the complement cascade. Another study showed that neutrophils of patients on IL-2 therapy expressed both phenotypic (up-regulation of CD11b/CD18 adhesion receptor expression) and functional (hydrogen peroxide and hypochlorous acid production) evidence of potent neutrophil activation.

Gut bacterial translocation is associated with chronic inflammatory states such as heart failure and mucositis, and acute states such as sepsis or GVHD, is translocation of bacterial flora into systemic circulation. Interestingly, IL-2 toxicity is associated with an interference with the gut flora and inflammation. In a recent study, 51 male rats were randomized to receive rIL-2 by intraperitoneal injection at doses (IU) of 10(5) (n=15), 10(4) (n=8), 10(3) (n=8) or 10(2) (n=8) twice daily, or a saline bolus (n=12). After 5 days, ileal histomorphology was assessed and the mesenteric lymph node complex was cultured. Results showed that colonisation of mesenteric lymph nodes with *Escherichia coli* occurred in all rats treated with 10(5) IU of rIL-2, and in 62%, 37% and 12% of rats treated with decreasing doses of rIL-2. No translocation was observed in control animals. An increase in submucosal lymphatics and occasional mucosal disruption was seen only in the group receiving 10(5) IU. These data show that rIL-2 promotes bacterial translocation and suggests a mechanism that may fuel high-dose rIL-2 toxicity in humans. Given the potent effects seen clinically with homeostatically-induced lymphocyte activation, and the recent findings that T cell homeostatic proliferation appears to be associated with gut flora translocation, it may be possible that tumor suppressive activity of IL-2 may be highly dependent on the gut flora, thus possibly explaining inter-patient variation.

Numerous studies have demonstrated that oxidative stress modifies endothelial cells in a manner that preferentially activates the complement cascade. The involvement of the mannose-binding lectin and the lectin complement pathway (LCP) in promoting complement activation by endothelial cells post oxidative stress was shown in studies using hypoxic (24 hours; 1% O(2))/reoxygenated (3 hours; 21% O(2)) human endothelial cells. Using iC3b deposition as a marker of complement activation, it was shown that N-acetyl-D-glucosamine or D-mannose, but not L-mannose, blocked activation, suggesting that oxidative stress upregulates the mannose dependent pathway. This was also demonstrated using mannose binding lectin deficient serum, as well as antibodies to mannose binding lectin. Furthermore C3 deposition was found in ischemic areas in rats that experienced cardiac ischemia reperfusion injury, a known inducer of oxidative stress.

It is documented that a scurvy-like condition occurs in a renal cell carcinoma patient treated with IL-2. The patient presented with acute signs and symptoms of scurvy (perifollicular petechiae, erythema, gingivitis and bleeding). Serum ascorbate levels were significantly reduced to almost undetectable levels during the treatment with IL-2. Although the role of ascorbic acid (AA) hyper-supplementation in stimulation of immunity in healthy subjects is controversial, it is well established that AA deficiency is associated with impaired cell mediated immunity. This has been demonstrated in numerous studies showing that deficiency of this vitamin suppresses T cytotoxic responses, delayed type hypersensitivity, and bacterial clearance. Additionally, it is well-known that NK activity, which mediates IL-2 anti-tumor activity, is suppressed during conditions of AA deficiency. Thus it may be that while IL-2 therapy on the one hand is stimulating T and NK function, the systemic inflammatory syndrome-like effects of this treatment may actually be suppressed by induction of a negative feedback loop. This negative feedback loop with IL-2 therapy was successfully overcome by work using low dose histamine to inhibit IL-2 mediated immune suppression, which led to the "drug" Ceplene (histamine dichloride) receiving approval as an IL-2 adjuvant for treatment of AML. Given the deficiency in endogenous ascorbic acid levels after IL-2 administration, the application seeks to overcome this deficit by prophylactically dosing the patient with ascorbic acid prior to, as well as concurrently with, and subsequently after immunotherapy.

The concept of AA deficiency subsequent to IL-2 therapy was reported previously by another group. Marcus et al evaluated 11 advanced cancer patients suffering from melanoma, renal cell carcinoma and colon cancer being on a 3 phase immunotherapeutic program consisting of: a) 5 days of i.v. high-dose (10(5) units/kg every 8 h) interleukin 2, (b) 6½ days of rest plus leukapheresis; and (c) 4 days of high-dose interleukin 2 plus three infusions of autologous lymphokine-activated killer cells. Mean plasma ascorbic acid levels were normal (0.64+/−0.25 mg/dl) before therapy. Mean levels dropped by 80% after the first phase of treatment with high-dose interleukin 2 alone (0.13+/−0.08 mg/dl). Subsequently plasma ascorbic acid levels remained severely depleted (0.08 to 0.13 mg/dl) throughout the remainder of the treatment, becoming undetectable (less than 0.05 mg/dl) in eight of 11 patients during this time. Importantly, blood pantothenate and plasma vitamin E remained within normal limits in all 11 patients throughout the phases of therapy, suggesting the hypovitaminosis was specific for AA. Strikingly, responders (n=3) differed from nonresponders (n=8) in that plasma ascorbate levels in the former recovered to at least 0.1 mg/dl (frank clinical scurvy) during Phases 2 and 3, whereas levels in the latter fell below this level. Similar results were reported in another study by the same group examining an additional 15 patients. The hypothesis that prognosis was related to AA levels is intriguing because of the possibility of higher immune response in these patients, however this has not been tested.

The main cause of VSL is increased permeability of the endothelium. Regardless of if the initiating cause is T cell activation, complement, and/or oxidative stress, the effector mechanism of VLS is alteration of endothelial cell function. In SIRS the endothelium is also the main effector causing lethality. Methods by which these cells are altered by both SIRS and IL-2 include: a) endothelial cell apoptosis, b) upregulation of adhesion molecules, and c) increased procoagulant state.

It was shown that in vitro administration of AA led to reduction of TNF-alpha induced endothelial cell apoptosis. The effect was mediated in part through suppression of the mitochondria-initiated apoptotic pathway as evidenced by reduced caspase-9 activation and cytochrome c release. Another study examined 34 patients with NYHA class III and IV heart failure who received AA or placebo treatment. AA treatment (2.5 g administered intravenously and 3 days of 4 g per day oral AA) resulted in reduction in circulating apoptotic endothelial cells in the treated but this was not observed in the placebo control group. Various mechanisms for inhibition of endothelial cell apoptosis by AA have been proposed including upregulation of the anti-apoptotic protein bcl-2 and the Rb protein, suppression of p53, and increasing numbers of newly formed endothelial progenitor cells.

AA has been demonstrated to reduce endothelial cell expression of the adhesion molecule ICAM-1 in response to TNF-alpha in vitro in human umbilical vein endothelial (HUVEC) cells (HUVEC). By reducing adhesion molecule expression, AA suppresses systemic neutrophil extravasation during sepsis, especially in the lung. Other endothelial effects of AA include suppression of tissue factor upregulation in response to inflammatory stimuli, an effect expected to prevent the hypercoaguable state. Furthermore, ascorbate supplementation has been directly implicated in suppressing endothelial permeability in the face of inflammatory stimuli, which would hypothetically reduce vascular leakage. Given the importance of NF-kappa B signaling in coordinating endothelial inflammatory changes, it is important to note that AA at pharmacologically attainable concentrations has been demonstrated to specifically inhibit this transcription factor in endothelial cells. Several pathways of inhibition have been identified including reduction of i-kappa B phosphorylation and subsequent degradation, and suppression of activation of the upstream p38 MAPK pathway. In vivo data in support of eventual use in humans has been reported showing that administration of 1 g per day AA in hypercholesterolemic pigs results in suppression of endothelial NF-kappa B activity, as well as increased eNOS, NO, and endothelial function. In another porcine study, renal stenosis was combined with a high cholesterol diet to mimic renovascular disease. AA administered i.v. resulted in suppression of NF-kappa B activation in the endothelium, an effect associated with improved vascular function.

The possibility that IL-2 therapy induces a state of systemic inflammation similar to SIRS has been discussed previously. One of the fundamental questions is whether AA actually has beneficial effects on the process of systemic inflammation. A mouse study demonstrated that after challenge with the bacteria *Klebsiella pneumonia* to induce a sepsis-like state, a 3-fold higher mortality is observed in ascorbate-deficient animals compared to controls. Another study hyper-supplemented animals with AA by administration of 10 mg/kg AA intravenously before induction of sepsis. IV AA treated animals had a 50% survival while only 19% of control animals survived. Other studies demonstrated that hyper-supplementation with AA resulted in better outcomes in sepsis-associated hypoglycemia, microcirculatory abnormalities, and blunted endothelial responsiveness in animal models.

Randomized clinical trials have been performed in septic patients using AA and vitamin E, which demonstrated superior outcomes, as well as reduction in parameters of oxidative stress. To date we know of one study in the recent history that assessed AA alone in patients with systemic inflammation. The investigators examined burn patients with >30% of their total body surface area affected. Patients were administered intravenous AA i.v. (66 mg/kg/hr for 24 hours, n=19) or received only standard care (controls, n=18). AA treatment resulted in statistically significant reductions in 24 hr total fluid infusion volume, and fluid retention (indicative of vascular leakage). Perhaps most striking was the decrease in the need for mechanical ventilation: the treated group required an average of average of 12.1±8.8 days, while the control group required 21.3±15.6 days. Given that numerous inflammatory markers associated with VLS are also found in SIRS and severe burn patients, the possibility is presented that AA may exert some beneficial effects on IL-2 therapy, both from the reduction of toxicity perspective, as well as from the stimulation of efficacy. Given the similarity between immunotherapy associated toxicity and SIRS, and given the ability to inhibit SIRS by administration of antioxidants, the current application teaches the use of antioxidants as a means of decreasing toxicities associated with immunotherapy, particularly, IL-2 administration.

Example

Female C57/BL6 mice are administered 5×10$^5$ B16 melanoma cells (American Type Culture Collection (Manassas, Va.)) cells subcutaneously into the hind limb flank. Mice are divided into groups of 12 mice per group as follows: a) saline administered intravenously, 200 microliters once every two days; b) IL-2 administered intravenously at 1000 IU every two days; c) ascorbic acid administered at 50 mg intravenously every second day; and d) ascorbic acid administered together with IL-2 intravenously every second day. Intravenous administration was performed into the tail vein. Tumor growth was assessed every 3 days by two measurements of perpendicular diameters by a caliper, and animals were sacrificed when tumors reached a size of 1 cm in any direction. Tumor volume was calculated by the following formula: (the shortest diameter$^2$× the longest diameter)/2. As observed in FIG. 1, a synergistic decrease of tumor growth was observed in the combination of IL-2 and intravenous ascorbic acid.

The invention claimed is:

1. A method of treating melanoma through administration of immune stimulant IL-2 in combination with an anti-cancer effective dose of an ascorbic acid antioxidant.

2. The method of claim 1, wherein the ascorbic acid is administrated at 50 mg/kg/hr.

3. The method of claim 1, wherein said administration occurs intravenously.

4. The method of claim 1, wherein cancer patients are treated by a treatment consisting essentially of the step of administering to the patient, by intravenous infusion, an anti-cancer effective dose of ascorbic acid or a pharmaceutically acceptable salt thereof together with IL-2.

5. The method of claim 4, wherein the intravenous infusion of ascorbic acid or a pharmaceutically acceptable salt thereof is administered over a period of at least two hours, prior to, concurrently with, or subsequently to administration of IL-2.

6. The method of claim 5, further comprising the step of determining the serum concentration of ascorbic acid that is effective at protecting the endothelium of said cancer patient from endothelial toxicity induced by IL-2, wherein said toxicity to endothelium of said patient is selected from a group consisting of: a) induction of endothelial cell apoptosis; b) stimulation of a thrombotic state in said endothelium; c) inhibition of anti-coagulant state of said endothelium; and d) induction of endothelial leakage.

7. The method of claim 5 further comprising the step of combining with the ascorbic acid, a tumor delivery agent.

8. The method of claim 5 further comprising the step of combining with the ascorbic acid, effective amounts of at least one agent selected from a group consisting of vitamin K, menadione, linolenic acid, linoleic acid, arachidonic acid, eicosapentaenoic acid, dihomogamma-linoleic acid, docosahexaenoic acid, eicosatetraenoic acid, sodium azide, copper, and iron to correct a deficiency of nutrients or micronutrients.

9. The method of claim 8 wherein the ascorbic acid is combined with tumor delivery effective amounts of hyaluronic acid.

* * * * *